(12) United States Patent
Moulton et al.

(10) Patent No.: US 10,518,960 B2
(45) Date of Patent: Dec. 31, 2019

(54) BAGS AND BAG-DISPENSING DEVICES AND METHODS OF USING SAME

(71) Applicants: Elizabeth B. Moulton, Pacific Palisades, CA (US); Caroline Park, El Segundo, CA (US); Deanna Griffith, El Segundo, CA (US); Daniel Ashcraft, El Segundo, CA (US); Britt Ashcraft, El Segundo, CA (US)

(72) Inventors: Elizabeth B. Moulton, Pacific Palisades, CA (US); Caroline Park, El Segundo, CA (US); Deanna Griffith, El Segundo, CA (US); Daniel Ashcraft, El Segundo, CA (US); Britt Ashcraft, El Segundo, CA (US)

( * ) Notice: Subject to any disclaimer, the term of this patent is extended or adjusted under 35 U.S.C. 154(b) by 553 days.

(21) Appl. No.: 15/069,643

(22) Filed: Mar. 14, 2016

(65) Prior Publication Data

US 2016/0264343 A1 Sep. 15, 2016

Related U.S. Application Data

(60) Provisional application No. 62/132,069, filed on Mar. 12, 2015.

(51) Int. Cl.
| | |
|---|---|
| *B65D 83/08* | (2006.01) |
| *B65D 33/16* | (2006.01) |
| *B65D 33/00* | (2006.01) |
| *A61F 13/551* | (2006.01) |
| *B65B 7/08* | (2006.01) |
| *B65D 33/24* | (2006.01) |
| *B65D 33/25* | (2006.01) |

(52) U.S. Cl.
CPC ........ *B65D 83/0805* (2013.01); *A61F 13/551* (2013.01); *B65B 7/08* (2013.01); *B65D 33/002* (2013.01); *B65D 33/007* (2013.01); *B65D 33/1658* (2013.01); *B65D 33/24* (2013.01); *A61F 2013/55195* (2013.01); *B65D 33/2508* (2013.01)

(58) Field of Classification Search
CPC .............. B65D 83/0805; B65D 33/002; B65D 33/2508; A61F 13/551; A61F 2013/55195
USPC ............. 383/33; 53/469, 459; 206/286, 554, 206/229; 248/99
See application file for complete search history.

(56) References Cited

U.S. PATENT DOCUMENTS

| | | | |
|---|---|---|---|
| 3,589,595 A | 6/1971 | White | 383/11 |
| 3,646,723 A * | 3/1972 | Meroney | B65B 67/1266 141/390 |
| 4,106,733 A * | 8/1978 | Walitalo | B65B 67/1266 248/100 |
| 5,000,582 A | 3/1991 | Pierson | 383/7 |

(Continued)

*Primary Examiner* — Robert F Long
*Assistant Examiner* — Xavier A Madison
(74) *Attorney, Agent, or Firm* — Norton Rose Fulbright US LLP

(57) ABSTRACT

Methods, apparatuses, and systems for dispensing a bag which are configured to receive and retain one or more objects. Some bag dispenser embodiments can comprise a pair of guiderails angled toward each other so that a bag positioned between the two guiderails can slide along guiderails to press open the mouth of bag. Other dispensers can comprise a pair of guiderails that are parallel. Other embodiments of the present disclosure comprise bags that are configured for use with the dispenser. Still other embodiments are described.

20 Claims, 11 Drawing Sheets

(56) References Cited

U.S. PATENT DOCUMENTS

| | | | |
|---|---|---|---|
| 5,044,774 A | 9/1991 | Bullard et al. | 383/34.1 |
| 5,647,670 A | 7/1997 | Iscovich | 383/33 |
| 6,286,681 B1 | 9/2001 | Wilfong, Jr. et al. | 206/554 |
| 6,505,750 B1 | 1/2003 | Nguyen | 211/163 |
| 6,799,695 B1 | 10/2004 | Borrero | 221/59 |
| 6,827,491 B2 | 12/2004 | Kohl et al. | 383/64 |
| 8,210,354 B2 | 7/2012 | Alvarado et al. | 206/554 |
| 2006/0106357 A1 | 5/2006 | McLean | 604/385.02 |
| 2008/0212903 A1* | 9/2008 | Germanow | A61F 13/551 383/42 |
| 2008/0247679 A1 | 10/2008 | Dayton et al. | 383/33 |
| 2008/0310772 A1 | 12/2008 | Dayton et al. | 383/61.1 |
| 2013/0223766 A1 | 8/2013 | Gebhardt | 383/6 |

* cited by examiner

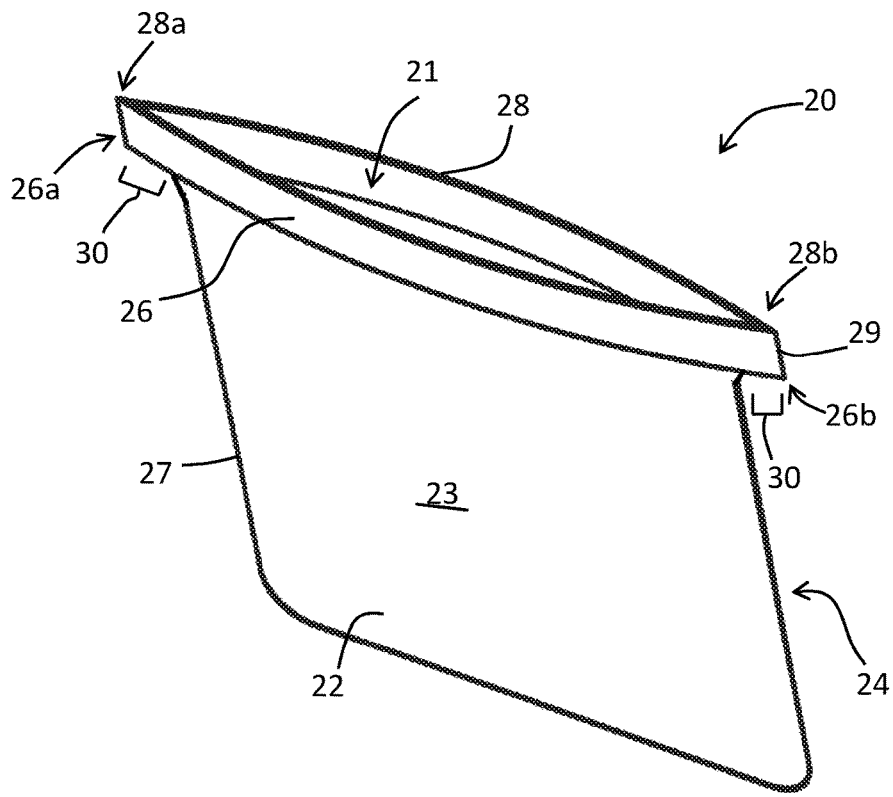
FIG. 4C
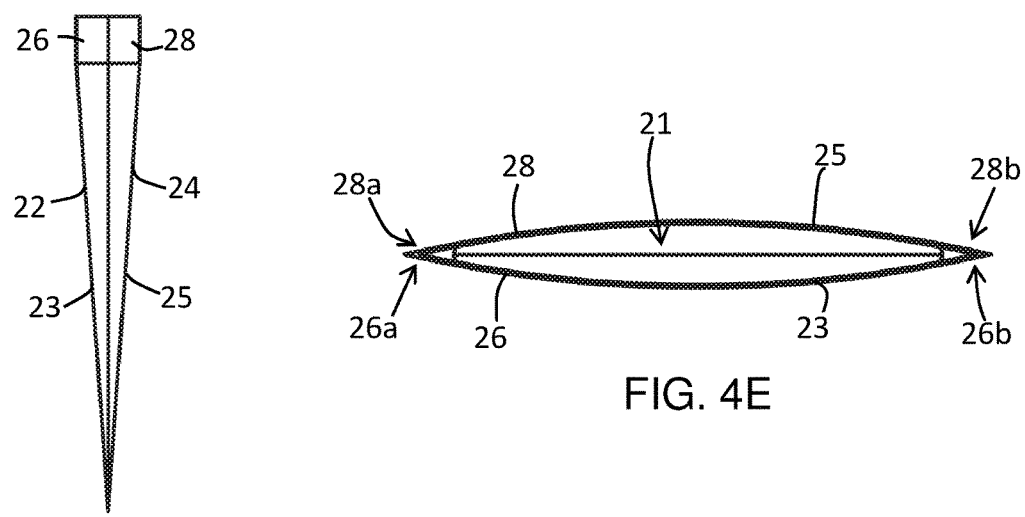
FIG. 4D
FIG. 4E

BAGS AND BAG-DISPENSING DEVICES AND METHODS OF USING SAME

CROSS REFERENCE TO RELATED APPLICATION

This application claims the benefit of U.S. Provisional Application No. 62/132,069, filed Mar. 12, 2015, which is incorporated by reference herein

FIELD OF THE INVENTION

The present inventions relate generally to bags and bag dispensers and, more particularly, but not by way of limitation, to apparatuses, kits, and methods for dispensing a bag.

BACKGROUND

Consumers commonly use bags for storing or disposing of objects, such as food products or waste products. Most bags do not have closure mechanisms such that any contents in the bag are securely retained therein. And those that do have a closure mechanism do not provide an easy manner of opening and closing and an orderly manner of dispensing. Bags that are intended to be single use bags that are easy to access, such as through a dispenser, and easy to close after filling can be beneficial.

Moreover, in situations where the bag requires one or more hands to hold the bag open while placing an object or objects in the bag, the task can be difficult or less efficient to manage by a single individual. In some situations, one may not wish to touch the bag to hold the bag open while filling the bag. Bags and bag dispensers that can facilitate the opening and filling process can be beneficial.

SUMMARY

This disclosure includes embodiments for a bag dispenser and bags that can be used with the bag dispenser and methods of using the same. Some embodiments of the present disclosure include a bag dispenser with a set of guiderails that are spaced apart from each other but the distance between the guiderails is not constant. Instead, at least on a section of the set of guiderails, the distance between the guiderails narrows in a manner that facilitates the mouth of a bag being pressed open as it is drawn along this narrowing section of guiderails.

Some embodiments of the present disclosure can comprise a bag dispenser that has first and second guiderails spaced apart and each extending between a rear-end and a front-end. The first and second guiderails are disposed such that a first distance between the guiderails at their rear-ends is greater than a second distance between the guiderails at at least one point between the rear-ends and the front-ends (or vice versa). The bag dispenser can further comprise first and second stops, each being disposed along one of the first and second guiderails. The first and second stops are configured to resist sliding movement of a bag supported by the guiderails. Moreover, the first and second stops are spaced apart a third distance that is less than the first distance. In some embodiments, each guiderail comprises a guiding surface and a supporting surface, where the guiding surface extends along the supporting surface and is configured to compress a portion of the bag as the bag is drawn toward the front end of the guiderails. In some embodiments, the guiderails are disposed in a housing. In some embodiments, a bag is disposed between the guiderails.

Some embodiments of the present disclosure can comprise a bag having opposing side panels defining a mouth. The bag can further comprise semi-rigid bands that are coupled to upper portions of the opposing side panels adjacent the mouth. The bands can be laterally extending or rather extend from side-to-side. During use, the bands would extend between the guiderails and a first and second end of each band would be supported by a corresponding one of the supporting surfaces of the guiderails. Here the third distance is small enough to prevent straightening of the bands and thereby to hold the mouth of the bag open, further comprising at least a first bag and a second bag disposed between the stops and the rear-ends such that an opposing panel of the first bag is facing an opposing panel of the second bag.

Some embodiments of the present disclosure can comprise a bag having opposing side panels defining a mouth. The bag can further comprise semi-rigid bands that are coupled to upper portions of the opposing side panels adjacent the mouth. The bands can be laterally extending or rather extend from side-to-side. During use, the bands would extend between the guiderails and a first and second end of each band would be supported by a corresponding one of the supporting surfaces of the guiderails. Here the third distance is small enough to prevent straightening of the bands and thereby to hold the mouth of the bag open, further comprising at least a first bag and a second bag disposed between the stops and the rear-ends such that an opposing panel of the first bag is facing an opposing panel of the second bag.

Particular embodiments of the present devices comprise first and second curved guiderails that converge toward each other but do not necessarily merge. A bag in a closed configuration can be placed at a starting position in the dispenser between the first and second guiderails and drawn into an open configuration as the bag slides along the guiderails from the starting position to an ending position between converging portions of the guiderails. Moreover, first and second stops are each disposed along one of the first and second guiderails and configured to resist sliding movement of the bag supported by the guiderails.

Other embodiments of the present disclosure comprise a refill set of bags where each bag comprises opposing side panels defining a mouth and semi-rigid bands coupled to upper portions of the opposing side panels adjacent the mouth. In some embodiments, the bags are stacked such that an opposing side panel of one bag is adjacent and substantially coextensive with an opposing panel of a neighboring bag, where each bag is releasably coupled to a neighboring bag, such as in the vicinity of the semi-rigid bands. In other embodiments, a refill set of bags can also comprise bags where each bag comprises opposing side panels defining a mouth and a foldable band coupled to an upper portion of one of the opposing side panels adjacent the mouth.

Still other embodiments of the present disclosure comprise methods of using the bags. In some embodiments, a method of opening a bag can comprise drawing a bag in a rear-to-front direction between two converging surfaces, wherein drawing the bag causes an inwardly facing force to be applied to each lateral surface of the bag and an outwardly facing force to be applied to the rear surface of the bag, thereby forcing the mouth to open. In some embodiments, a method of closing the bag can comprise drawing the bag in a front-to-rear or rear-to-front direction, wherein drawing the bag in a rear-to-front or front-to-rear direction causes a reduction in an inwardly facing force applied to each lateral surface of the bag, thereby causing the mouth to close. The described bags and bag dispenser can be adapted for packaging or for disposal. The mouth of the bag can be configured to securely close or seal such that any contents in the bag are securely retained therein. In particular embodiments, a used hygiene product can be placed in the bag when bag is pressed open by the guiderails and then closed and disposed of, such as in a trash receptacle.

The term "coupled" is defined as connected, although not necessarily directly, and not necessarily mechanically; two items that are "coupled" may be unitary with each other. The terms "a" and "an" are defined as one or more unless this disclosure explicitly requires otherwise. The term "substantially" is defined as largely but not necessarily wholly what is specified (and includes what is specified; e.g., substantially 90 degrees includes 90 degrees and substantially parallel includes parallel), as understood by a person of ordinary skill in the art. In any disclosed embodiment, the terms "substantially," "approximately," and "about" may be substituted with "within [a percentage] of" what is specified, where the percentage includes 0.1, 1, 5, and 10 percent.

Further, a device or apparatus that is configured in a certain way is configured in at least that way, but it can also be configured in other ways than those specifically described.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a device or apparatus that "comprises," "has," "includes" or "contains" one or more elements possesses those one or more elements, but is not limited to possessing only those elements. Likewise, a method that "comprises," "has," "includes" or "contains" one or more steps possesses those one or more steps, but is not limited to possessing only those one or more steps.

Any embodiment of any of the device, apparatuses, kits, and methods can consist of or consist essentially of—rather than comprise/include/contain/have—any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb.

The feature or features of one embodiment may be applied to other embodiments, even though not described or illustrated, unless expressly prohibited by this disclosure or the nature of the embodiments.

Details associated with the embodiments described above and others are described below.

BRIEF DESCRIPTION OF THE DRAWINGS

The following drawings illustrate by way of example and not limitation. For the sake of brevity and clarity, every feature of a given structure is not always labeled in every figure in which that structure appears. Identical reference numbers do not necessarily indicate an identical structure. Rather, the same reference number may be used to indicate a similar feature or a feature with similar functionality, as may non-identical reference numbers. The figures are drawn to scale for at least the embodiments shown.

FIG. 1B(i) depicts an enlarged view of the boxed section in FIG. 1B.

FIGS. 4A-4G depict various views of an embodiment of a bag configured for use with a bag dispenser in accordance with the present disclosure. FIG. 4A shows a perspective view and FIG. 4B shows a front view of the bag in a closed conformation. FIG. 4C shows a perspective view, FIG. 4D shows a side view, and FIG. 4E shows a top view of the bag where the mouth of the bag is slightly open. FIG. 4F shows a perspective view and FIG. 4G shows a top view of the bag with the mouth of the bag in an opened conformation.

FIG. 6A depicts a front, perspective view. FIG. 6B depicts a rear perspective view. FIG. 6C depicts a perspective view of a manufacturing precursor of the bag, which can be folded along the dashed lines to form the bag.

DESCRIPTION OF ILLUSTRATIVE EMBODIMENTS

Figure 1A:
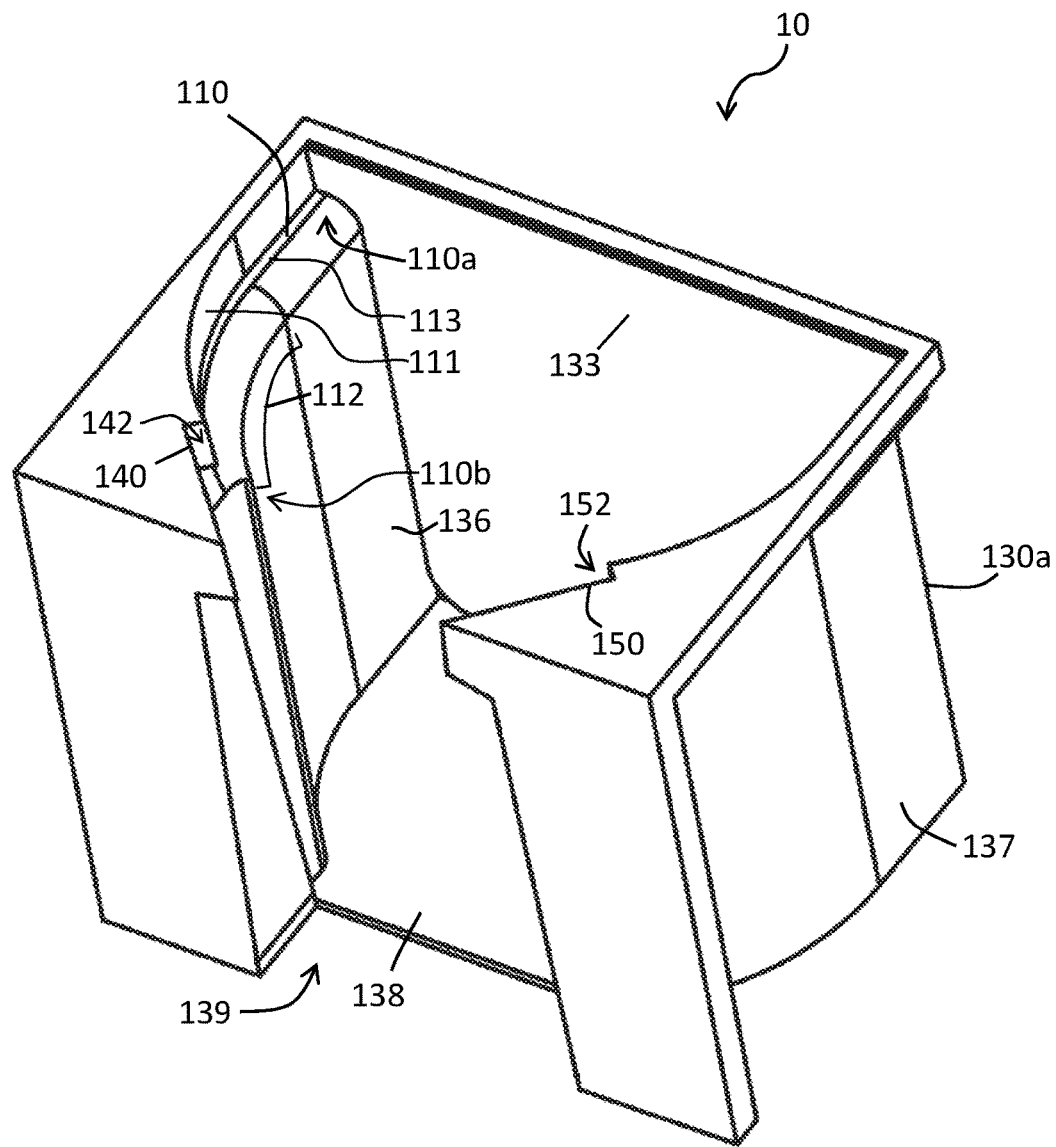
FIG. 1A and FIG. 1B, respectively, depict perspective and top views of an embodiment of a bag dispenser.

Referring now to the drawings and more particularly to FIGS. 1A-1B, 2, and 3A-3B, shown there and designated by the reference numeral 10 are embodiments of the present bag dispenser. In the embodiments shown, bag dispenser 10 comprises a pair of guiderails, including a first guide rail 110 and a second guiderail 120, angled toward each other so that a bag 20 positioned between the two guiderails 110, 120 can slide along guiderails 110, 120 to press open the mouth 21 of bag 20. In the embodiment shown, a section 112 of first guiderail 110 is angled toward a section 122 of second guiderail 120 so that a bag 20 in a closed configuration may be placed at a starting first position "A" between guiderails 110, 120 and drawn into an open configuration as the bag slides from the first position A along sections 112, 122 toward a second position "B", as described in more detail below.

Figure 1B:
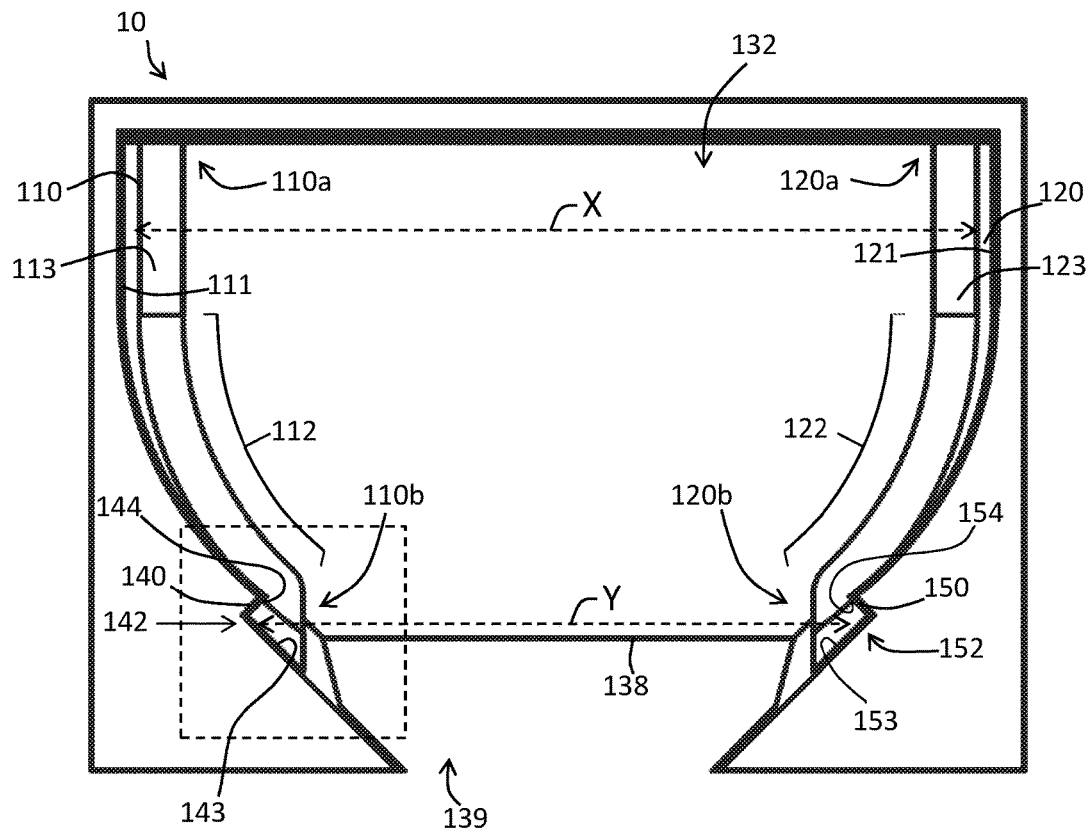
Figure 1B:
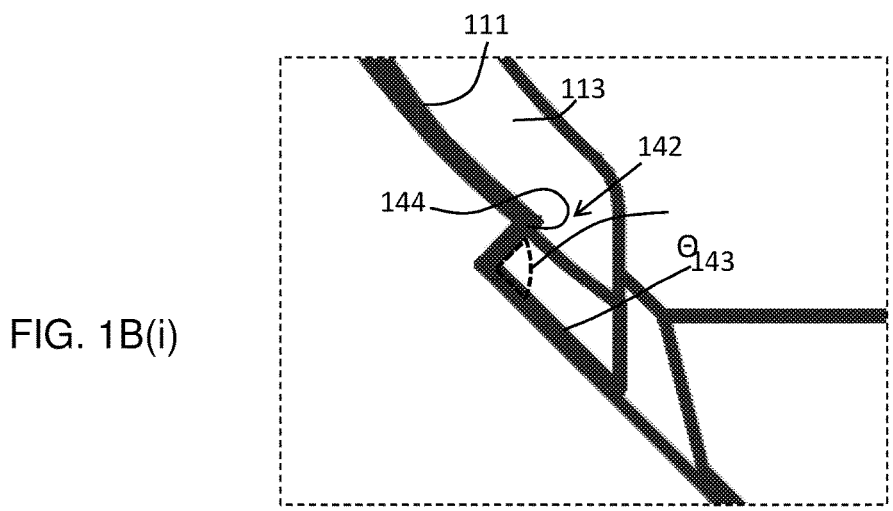
Figure 2:
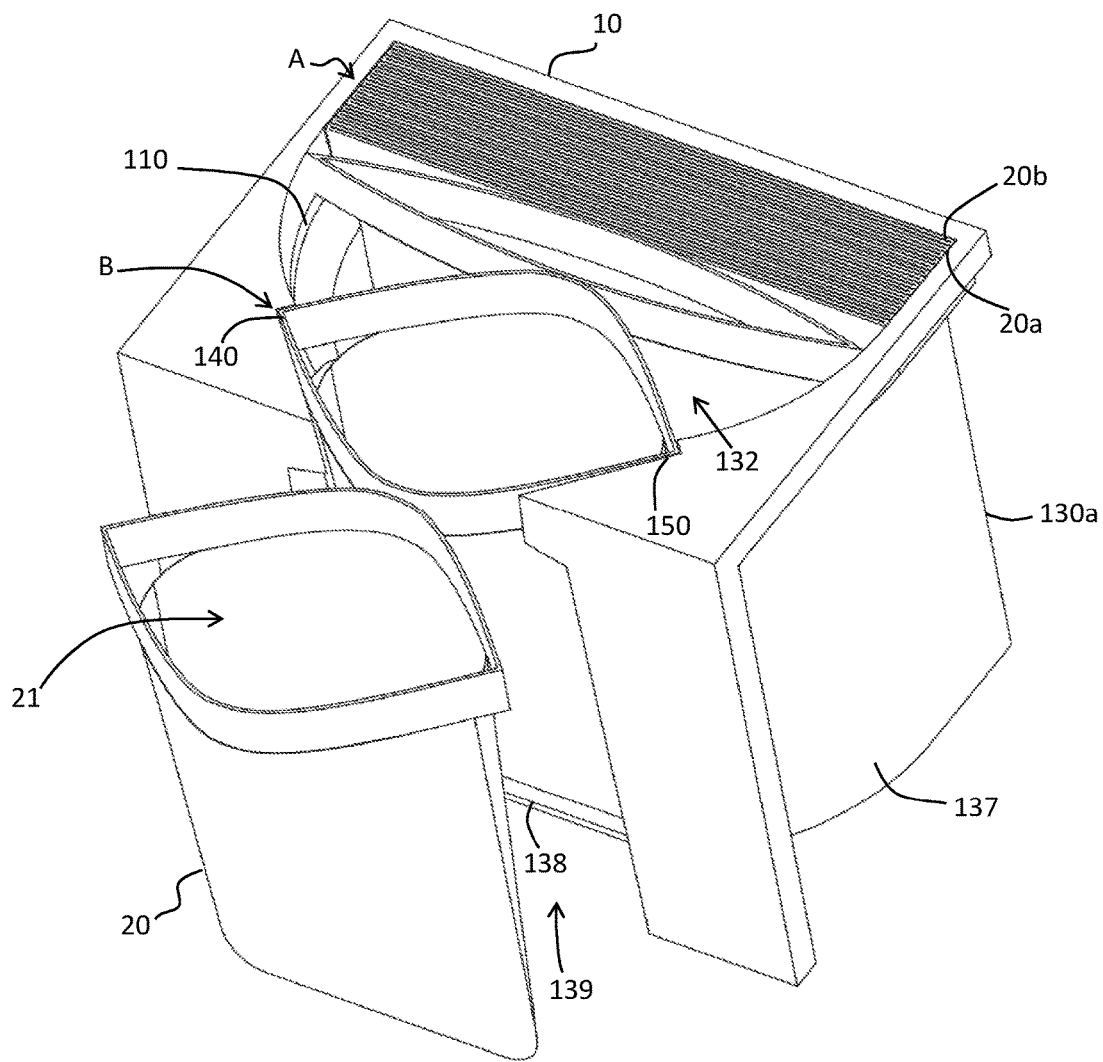
FIG. 2 depicts a perspective view of the embodiment of FIGS. 1A and 1B with a plurality of bags disposed in the bag dispenser.

In the embodiments shown, bag dispenser 10 comprises a housing 130a, 130b (collectively referred to as housing 130) within which the guiderails 110, 120 are disposed. A bag 20 can be removed through an opening (such as opening 132 and/or opening 139) in housing 130. FIGS. 1A-1B and 2 show an embodiment in which opening 132 is open at the front of the dispenser (e.g., does not have a closed upper perimeter) and a bag 20 can be received through a first opening 132 located at an upper face of housing 130a and can be removed through a lateral, second opening 139 in housing 130a.

Figure 3A:
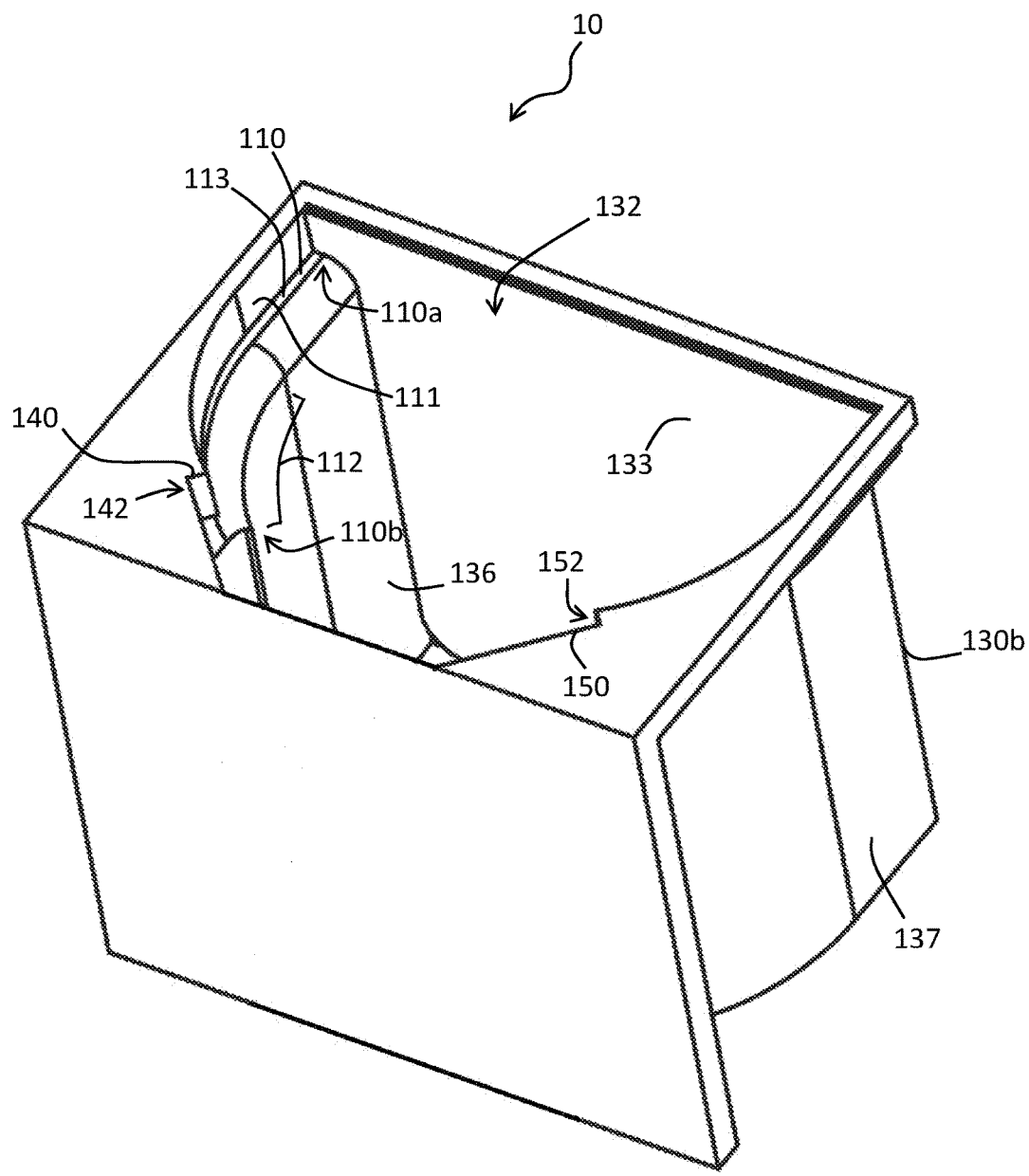
FIG. 3A and FIG. 3B, respectively, depict perspective and top views of another embodiment of a bag dispenser.
Figure 3B:
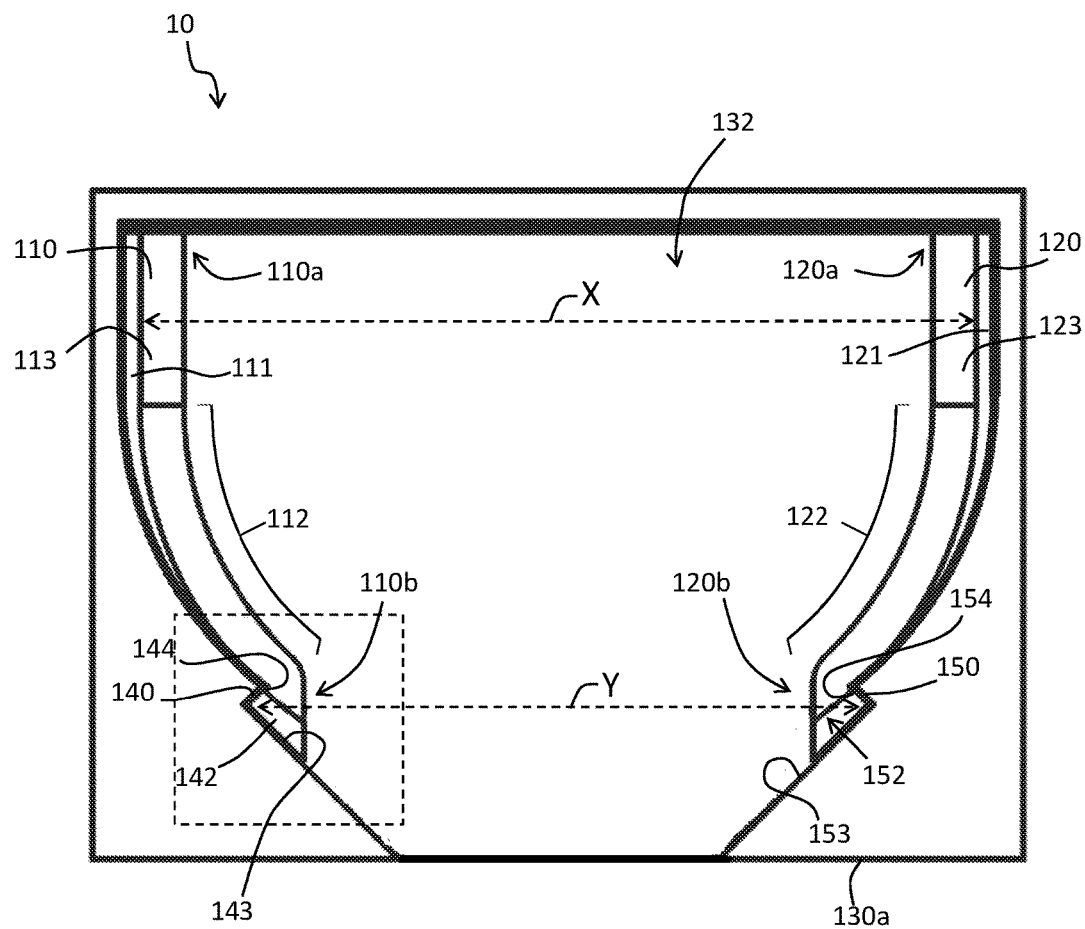
Figure 4A:
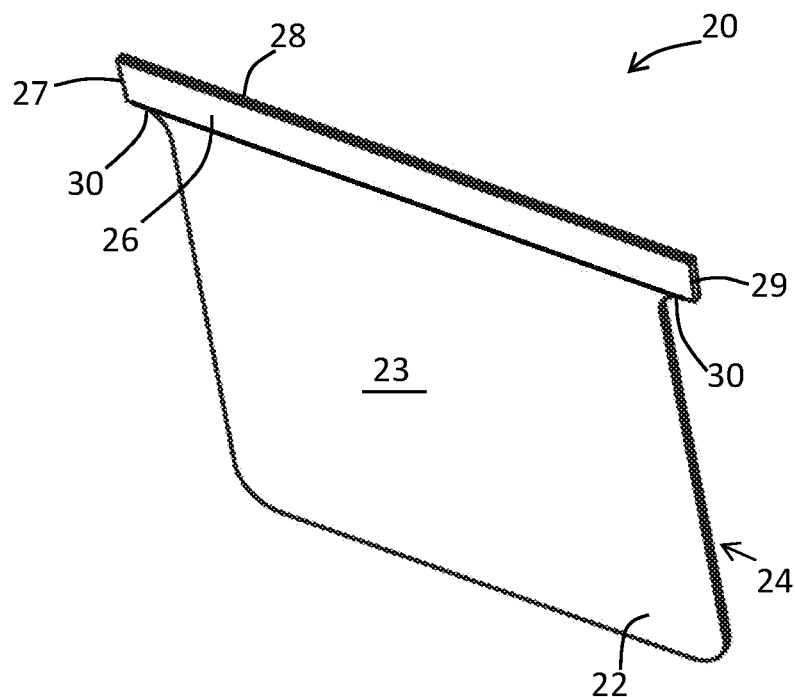
Figure 4B:
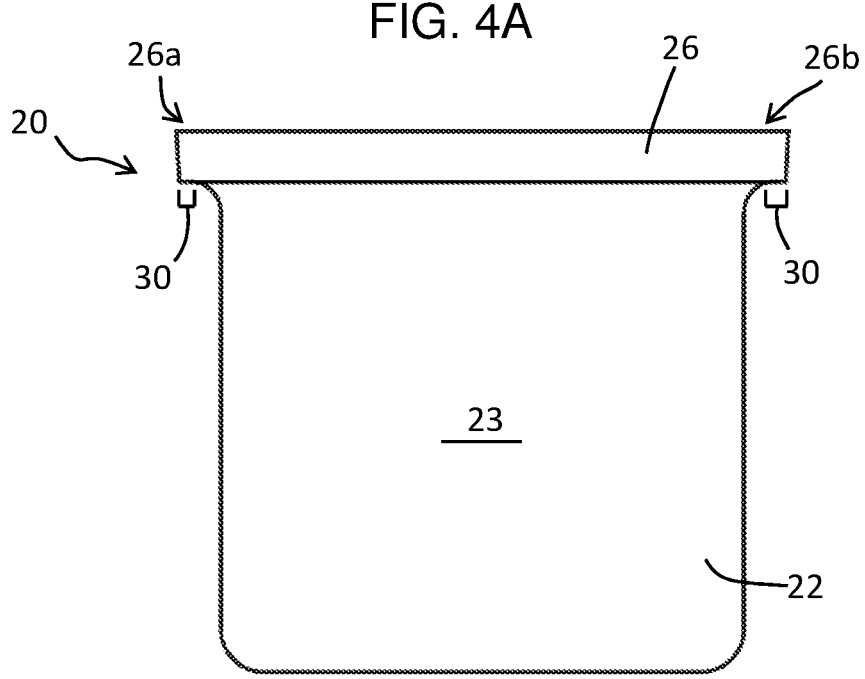
Figure 4F:
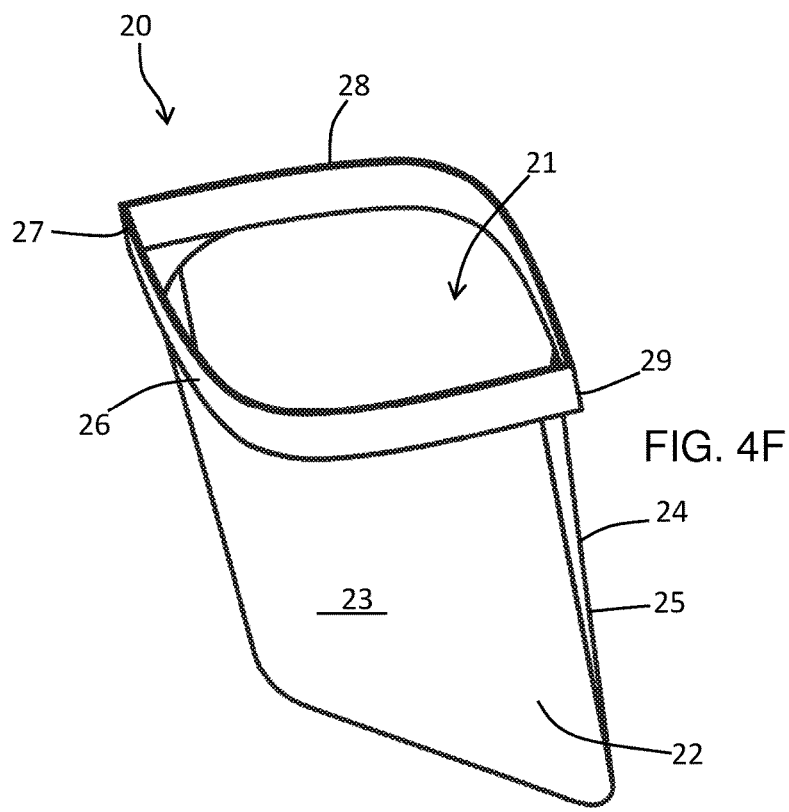
Figure 4G:
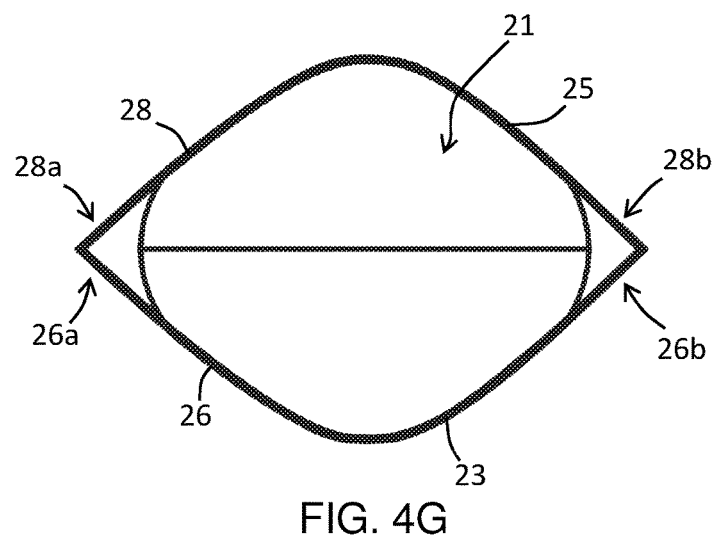

FIGS. 3A-3B show an embodiment, having a front wall 131 that defines a portion of a closed upper perimeter of opening 132, in which bag 20 can be received and removed through opening 132 located at an upper face of housing 130b. In such embodiments, to remove bag 20 from opening 132, bag 20 can be drawn from second position B back toward first position A, whereby the compression on bag 20 is removed/reduced and the mouth 21 of bag 20 is narrowed in the front to back direction. In various embodiments, to remove bag 20 from opening 139, bag 20 can be drawn from second position B frontward through opening 139, whereby the compression on bag 20 is removed/reduced and the mouth 21 of bag 20 is narrowed in the front to back direction.

In the embodiments shown, first and second guiderails 110, 120 are spaced apart from one another and each extend between respective rear ends 110a, 120a and front ends 110b, 120b. First and second guiderails 110, 120 are disposed such that a first distance "X" between guiderails 110, 120 at or near their rear-ends 110a, 120a is greater than a second distance "Y" between guiderails 110, 120 at or near at least one point between rear-ends 110a, 120a and front-ends 110b, 120b. For example, and as shown, at least a portion of guiderails 110, 120 can be arced or curved toward each other such that the guiderails are closer together near their front ends than at their rear ends. In other embodiments, first and second guiderails 110, 120 can each be straight and angle toward each other such that the guiderails are closer together near their front ends than at their rear ends.

In some embodiments, such as the one shown, each guiderail 110, 120 can comprise a guiding surface 111, 121 and a supporting surface 113, 123. Guiding surfaces 111, 121 can extend along supporting surface 113, 123 and can be configured to guide bag 20 as bag 20 is drawn toward front ends 110b, 120b of guiderails 110, 120. Guiding surfaces 111, 121 are configured to compress a portion of bag 20 when bag 20 is drawn toward front ends 110b, 120b of guiderails 110, 120. For example, guiding surfaces 111, 121 can face inward and toward each other or slightly rearward. Supporting surfaces 113, 123 are configured to support bag 20 so that the upright orientation of bag 20 is maintained when disposed therein. For example, supporting surfaces 113, 123 can face generally upward. In some embodiments, supporting surfaces 113, 123 can also be substantially coplanar to each other.

In various embodiments, each guiding surface 111, 121 can extend above (or below) and along the length of a corresponding one of supporting surfaces 113, 123. In certain embodiments, guiding surfaces 111, 121 or at least the vertical portions of guiding surface 111, 121 can be substantially perpendicular to the corresponding supporting surface 113, 123 or at least to the horizontal portions of the corresponding supporting surface 113, 123.

Bag dispenser 10 can also comprise stops 140, 150 on one or both (as shown) of guiderails 110, 120. In the embodiments shown, a first stop 140 is disposed along first guiderail 110, and a second stop 150 is disposed along second guiderail 120. First and second stops 140, 150 can be configured to resist sliding movement of bag 20 when supported by guiderails 110, 120, and more particularly to resist sliding movement back toward the first position A. For example, one or both of stops 140, 150 can comprise or define a recess 142, 152, as shown, in a corresponding one of guiding surfaces 111, 121 and/or supporting surfaces 113, 123. In the embodiment shown, the distance Y between first and second stops 140, 150 is less than the first distance X. In the embodiments shown, each supporting surface 113, 123 extends at least partially into the recess of the corresponding one of the first and second stops 140, 150.

In various embodiments, recesses 142, 152 can each be defined by two surfaces, namely a rearward-facing surface 143 or 153 and a frontward-facing surface 144 or 154, that define an angle Θ (FIG. 1B(i)). In various embodiments, angle Θ generally corresponds to the angle that bands 26, 28 of bag 20 define at each end when bag 20 extends between stops 140, 150. In various embodiments, rearward-facing surfaces 143, 153 extend generally frontward (toward the front of the dispenser) to serve as a backstop for front-facing upper band 26 of bag 20. Similarly, though to a lesser degree in the depicted embodiments, frontward-facing surface 144, 154 can extend generally rearward and also serve as a stop for the rear-facing upper band 28 of bag 20.

In various embodiments, guiderails 110, 120 can further comprise a second section (not shown) that extends between stops 140, 150 and a front end. Corresponding second sections are angled away from each other so that a bag positioned between the two guiderails at second position B (e.g., at stops 140, 150) can slide along the guiderails to a third, more frontward position than position B, whereby the compression on the bag is removed/reduced so that the mouth of the bag can be narrowed (e.g., partially closed).

In various embodiments, bag dispenser 10 can further comprise housing 130 that defines an interior volume 134 and at least one opening (e.g., opening 132) where the first and second guiderails 110, 120 are disposed in interior 134 of housing 130. In some embodiments, housing 130 comprises a first sidewall 136, an opposing a second sidewall 137, a base 138 opposite opening 132. In some embodiments, first and second guiderails 110, 120 are integrated into and/or unitary with the respective sidewalls 136, 137. In some embodiments, guiderails 110, 120 can be disposed closer to opening 132 than base 138.

In certain embodiments, opening 132 is dimensioned to allow bag 20 to pass through opening 132 at a location between stops 140, 150 and rear ends 110a, 120a of guiderails 110, 120. In some embodiments, opening 132 can be covered by a lid (not shown), which can, for example, be pivotally coupled to the housing via a hinge. In some embodiments, opening 132 can be located at the upper face of housing 130. Opening 132 can allow for one or more bags to be loaded into dispenser 10 and to be placed such that they extend between guiderails 110, 120. Opening 132 can also allow for a user to manually slide bag 20 from rear-ends 110a, 120a toward front-ends 110b, 120b, such as from first position A to second position B and/or from second position B to a third, more frontward position. In some embodiments, such as that of FIGS. 3A-3B, opening 132 can also allow for manual removal of bag 20 either pre- or post-filling.

With specific reference to FIGS. 1A-1B and 2, in various embodiments, housing 130 can further comprise a second opening 139 configured for a bag exit, typically post-filling. For example, in the embodiment shown, housing 130 can comprise a rear-end wall 133 and second opening 139 opposite the rear-end wall. Second opening 139 can be dimensioned to allow bag 20, particularly post-filling, to pass therethrough. In some embodiments, bag 20 can be manually pulled through second opening 139. In some embodiments, second opening 139 can be merged with opening 132 on the upper face of housing 130.

In yet other embodiments (not shown), second opening 139, or an additional third opening (not shown), can be defined through the bottom of container so that bag 20 exits through a bottom opening. In this way, dispenser 10 can be positioned directly over a trash can and bag 20 can fall directly into the trash can. In some embodiments, bag 20 can be drawn beyond front ends 110b, 120b of the supporting surfaces 113, 123 and thus bag 20 will fall through the base opening. In other embodiments, a portion of supporting surfaces 113, 123, such as in the vicinity of stops 140, 150 can be shiftable in an outward, frontward, and/or rearward direction sufficient so that supporting surfaces 113, 123 are not underneath any portion of bag 20. In such embodiments, portions of supporting surface 113, 123 adjacent stops 140, 150 can be moveable relative to housing and may be moveable relative to a corresponding portion of guiding surfaces 111, 121. An actuator button/lever can be coupled to shift supporting surfaces 113, 123 and configured to shift supporting surfaces 113, 123. Upon actuation, bag 20 will fall through the base opening.

In various embodiments, with reference to FIGS. 4A to 4G, bag 20 is configured to be received between first and second guiderails 110, 120 and slide along guiderails 110, 120 so that the mouth 21 of bag 20 will be pressed open. In some embodiments, bag 20 can comprise a front surface 23, an opposing rear surface 25, and two opposing lateral surfaces 27, 29. For example, bag 20 can comprise opposing panels 22, 24 defining mouth 21, and semi-rigid bands 26, 28 coupled to upper portions of the opposing side panels 22, 24. Semi-rigid bands 26, 28 can define or be adjacent to mouth 21. In certain embodiments, semi-rigid bands 26, 28 together can be two separate bands of material or can be coupled to each other so as to form a collapsed loop.

In various embodiments, semi-rigid bands 26, 28 are configured to extend between guiderails 110, 120 such that first ends 26*a*, 28*a* and second ends 26*b*, 28*b* of each band 26, 28 are supported by a corresponding one of supporting surfaces 113, 123. For example, the length of each band 26, 28 is slightly less than the distance between guiding surfaces 111, 121 at first position A. In some embodiments, first ends 26*a*, 28*a* and/or second ends 26*b*, 28*b* of each band 26, 28 extend beyond opposing side panels 22, 24 so that one or both of bands 26, 28 comprise an overhang portion 30 on each side of bag 20. When disposed between guiderails, overhang portion 30 can be disposed above and supported by supporting surface 113, 123.

Bag 20 can be any variety of sizes or shapes. The size and shape may depend on the intended use of bag 20. In some embodiments, bag 20 can have a width between 2 to 10 inches, such as 2, 3, 4, 5, 6, 7, 8, 9, or 10 inches, or any value therebetween, and a height between 2 to 10 inches, such as 2, 3, 4, 5, 6, 7, 8, 9, or 10 inches, or any value therebetween. An empty bag 20 can also have a depth (pre-filling) of 0.1, 0.3, 0.5, 0.8, 1, 2, 3, 4, or 5 inches, or any value therebetween. In addition, the distance between stops 140, 150, namely, distance Y, is small enough to prevent straightening of bands 26, 28 and thereby to hold mouth 21 of bag 20 open.

In various embodiments, bag 20 can be configured to facilitate opening of mouth 21 as bag 20 is drawn along narrowing first and second guiderails 110, 120. In some embodiments, semi-rigid bands 26, 28 can be biased to bow outward (e.g., away from each other) instead of bowing inward, upon applying compression between first ends 26*a*, 28*a* and second ends 26*b*, 28*b*, such as when bag 20 is drawn along narrowing first and second guiderails 110, 120. For example, semi-rigid bands 26, 28 can be slightly bowed in an outward direction relative to mouth 21 of bag 20. In some embodiments, a plurality of bags 20 can be stacked and releasably coupled to each other at band 26, 28 in order to facilitate opening mouth 21. For example, a plurality of bags 20 can be stacked such that opposing side panel 24 of one bag 20 is adjacent and substantially coextensive with opposing panel 22 of a neighboring bag 20. In some embodiments, each band 26, 28 is releasably coupled to a neighboring band. For example, in some embodiments, a restickable and/or releasable adhesive is disposed on at least a portion of one or both of the outwardly facing surfaces of bands 26, 28. In same or different embodiments, a first bag 20*a* is releasably coupled to a second bag 20*b* by a perforated member on each bag 20. In some embodiments, bands 26, 28 are releasable coupled to a neighboring band at an intermediate or central region of the outwardly facing surface of band 26, 28. In some embodiments, a set of bags 20 stacked and releasably coupled to each other can refill bag dispenser 10.

In various embodiments, bag 20 can be configured to securely close or seal. For example, in some embodiments, bands 26, 28 can couple to each other by way of a Ziploc style closure. In some embodiments, one or both of bands 26, 28 can comprise an adhesive that is covered with a removable protective strip. When a user goes to close or seal bag 20, the protective strip is pulled away from the adhesive and the inner surfaces of bands 26, 28 are pressed together.

Portions of bag 20 can be made of any suitable material. In some embodiments, semi-rigid bands 26, 28 can be made of, at least in part, a paper, metallic, or plastic material. More particularly, semi-rigid bands 26, 28 can be made of cardboard. In some embodiments, opposing panels 22, 24 are formed from the same or different material as semi-rigid bands 26, 28. Opposing panels 22, 24, or at least a portion thereof, can define at least a portion of the interior of bag 20 within which an object or objects can be placed. In some embodiments, opposing panels 22, 24 can be made of, at least in part, a plastic or paper material, e.g., wax paper. Opposing panels 22, 24 can comprise a substantially non-absorbent material. In some embodiments, bag 20 can include a fragrance, a deodorizer, and/or an antimicrobial agent.

In various embodiments, a method of opening a bag in accordance with the present disclosure can comprise drawing the bag in a rear-to-front direction between two converging surfaces, such as the guiding surfaces of the guiderails described herein. In certain embodiments, drawing the bag causes an inwardly facing force to be applied to each lateral surface of the bag, such as at the first ends and the second ends of the semi-rigid bands and also cause an outwardly facing force to be applied to the rear surface of the bag, thereby forcing the mouth to open. Conversely, in various embodiments, a method of closing the bag can comprise drawing a bag in a front-to-rear or rear-to-front direction between two converging surfaces, wherein drawing the bag in a rear-to-front or front-to-rear direction causes a reduction in an inwardly facing force applied to each lateral surface of the bag, thereby causing the mouth of the bag to narrow in a front to rear direction, i.e., become more closed. In embodiments, the method further comprises placing an object, such as a used hygiene product, in the bag when the mouth is in the open position. In embodiments, the mouth of the bag can be sealed such that any contents in the bag are securely retained therein.

Figure 5:
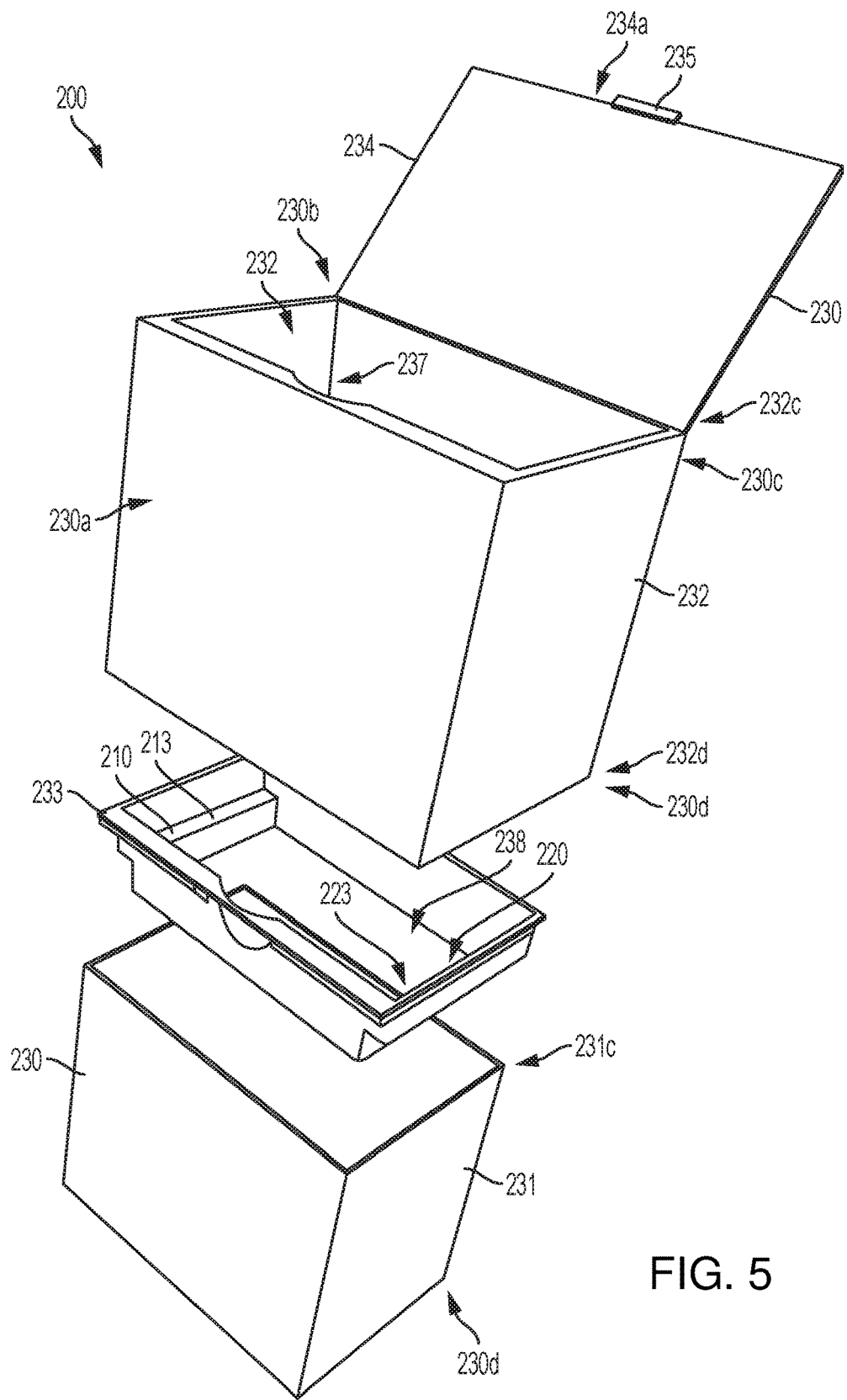
FIG. 5 depicts a perspective view of another embodiment of a bag dispenser.

Referring now to the drawings and more particularly to FIG. 5, another embodiment of a bag dispenser is shown. Bag dispenser 200 comprises a pair of guiderails, namely a first guide rail 210 and a second guiderail 220 spaced apart from each other so that a bag 300 can be supported by the two guiderails 210, 220 at the widest portion of the bag. Bag dispenser 200 can also comprise a housing 230 within which the guiderails 210, 220 are disposed and at least one opening 232 through which a bag 300 can be received and/or removed. In the embodiments shown, first and second guiderails 210, 220 are disposed such that they are parallel to each other and extend between a front end 230*a* of housing 230 and a rear end 230*b* of the housing. The first and second guiderails 210, 220 can also be parallel to the base 230*d* of housing 230.

Each guiderail 210, 220 can comprise a supporting surface 213, 223. Supporting surfaces 213, 223 are configured to support bag 300 so that an upright orientation of bag 300 is maintained when the bag is disposed thereon. For example, supporting surfaces 213, 223 can face generally upward. In some embodiments, supporting surfaces 213, 223 can also be substantially coplanar to each other.

As shown in FIG. 5, housing 230 can comprise an inner sleeve 231 and an outer sleeve 232 that fits over the inner sleeve 231. Inner sleeve 231 comprises guiderail 210, 220 at an upper end 231c and defines an opening at the upper end. Inner sleeve 231 is configured such that a plurality of bags can be disposed in an upright position, supported by guiderails 210, 220, within the inner sleeve and removed through the opening at the upper end 231c. Outer sleeve 232 defines an opening at a base 232d of the outer sleeve 232 and is configured to slide over and be disposed around inner sleeve 231, such that the inner sleeve can be nested within the outer sleeve. Outer sleeve 232 defines another opening at upper end 232c through which a bag disposed within the housing 230 can pass. Outer sleeve 232 comprises a lid 234 configured for moving to cover and uncover the opening at upper end 232c of outer sleeve 232. Lid 234 can comprise a tab 235 at a free end 234a that can be inserted into a cut-out/slot 237 on outer sleeve 232 and/or inner sleeve 231. The tab 235 and cut-out/slot 237 sized so that the tab frictionally fits into the cut-out/slot.

Guiderails 210, 220 can be located in an upper portion 230c of housing 230. Guiderails 210, 220 can be formed in lateral walls of housing 230 or be supported by the walls of housing 230. For example, as shown in FIG. 5, a frame 233, two opposing sides of which are guiderails 210, 220, can be configured to nest within inner sleeve 231 and be supported by upper end 231c of the inner sleeve. Frame 233 defines an opening 238 through which a bag can be inserted.

Figures 6A, 6B:
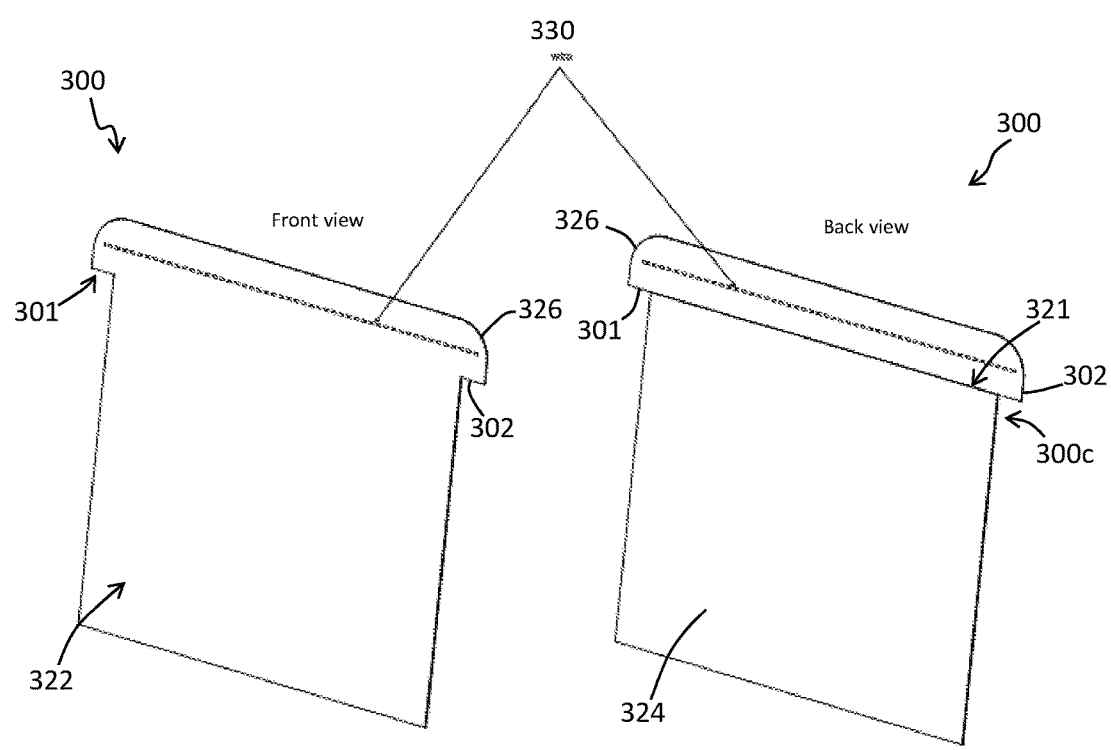
FIGS. 6A to 6C depict various views of an embodiment of a bag configured for use with a bag dispenser in accordance with the present disclosure.
Figure 6C:
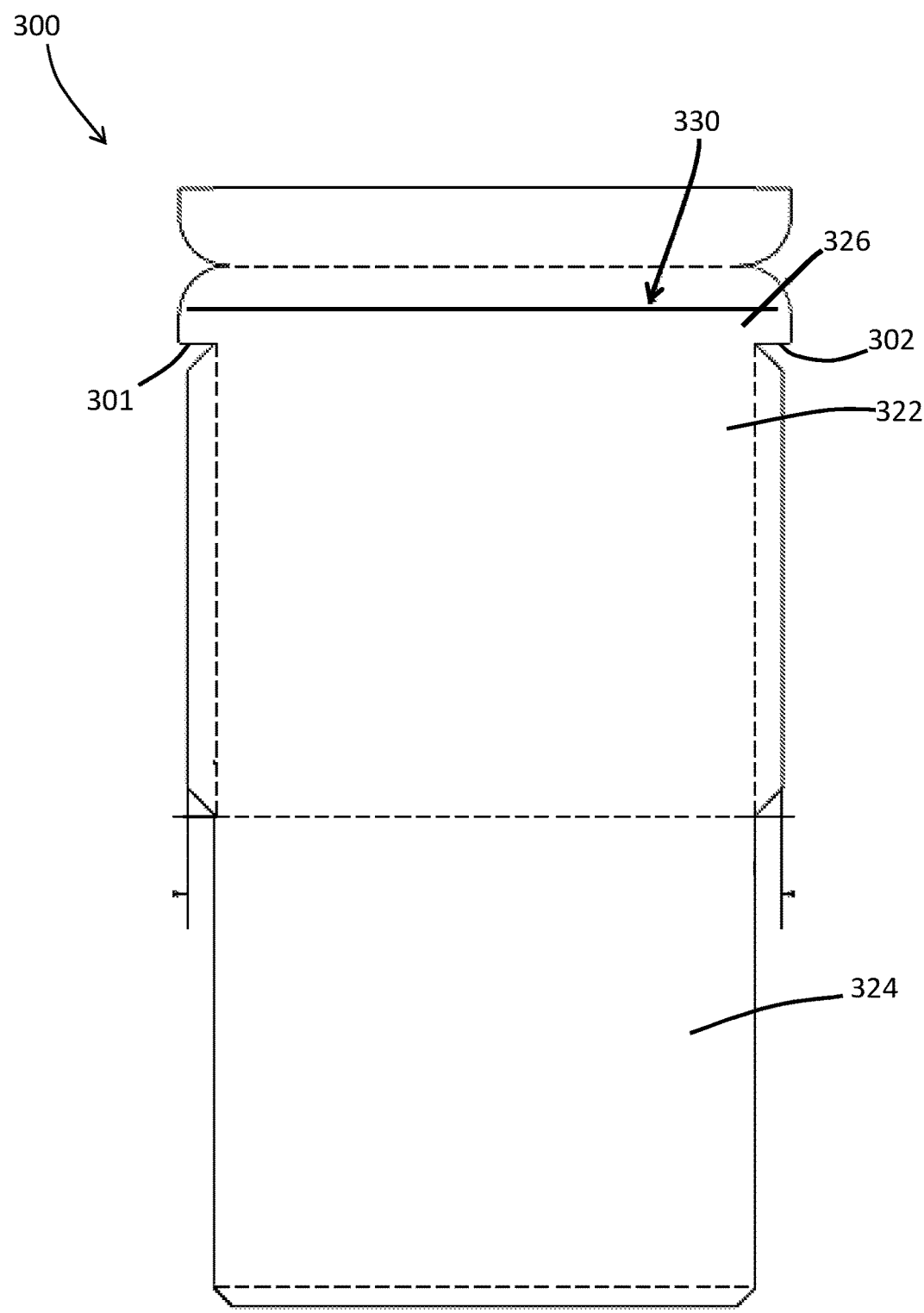

With reference to FIGS. 6A to 6C, another bag embodiment is shown. Bag 300 can be configured to be received between and supported by first and second guiderails 210, 220. In some embodiments, bag 300 can comprise a front panel 322 and an opposing rear panel 324. Opposing panels 322, 324 define a mouth 321 at an upper end 300c of bag 300.

Bag 300 is configured to seal so that solid contents can be contained therein. In the embodiment shown, a foldable band 326 is coupled to an upper portion of one of the opposing panels 322, 324. Foldable band 326 can define or be adjacent to mouth 321. Foldable band 326 is configured such that once folded it will retain its folded orientation; e.g., the band has low resilience. In some embodiments, foldable band 326 can comprise a wire 330 that extends along the length to facilitate the band retaining its folded orientation.

In various embodiments, foldable band 326 is configured to extend between guiderails 210, 220 and be supported by the supporting surfaces 213, 223 at each respective end of the foldable band. When disposed between guiderails 210, 220, an overhang portion 301, 302 of foldable band 326 can be disposed above and supported by supporting surface 213, 223, respectively.

Bag 300 can be any variety of sizes or shapes. The size and shape may depend on the intended use of bag 300. In some embodiments, bag 300 can have a width between 2 to 10 inches, such as 2, 3, 4, 5, 6, 7, 8, 9, or 10 inches, or any value therebetween, and a height between 2 to 10 inches, such as 2, 3, 4, 5, 6, 7, 8, 9, or 10 inches, or any value therebetween. An empty bag 300 can also have a depth (pre-filling) of 0.1, 0.3, 0.5, 0.8, 1, 2, 3, 4, or 5 inches, or any value therebetween. In some embodiments, the bag is configured to contain a used feminine hygiene product. For example, the interior volume of bag 300 may have an interior volume that is less than 300% or less than 200% of the volume of a feminine hygiene product.

Portions of bag 300 can be made of any suitable material like bag 20 described above. In some embodiments, foldable band 326 can be made of, at least in part, a paper, metallic, or plastic material. For example, foldable bands 326 can be made of cardboard or a combination of cardboard and a metallic wire. In some embodiments, opposing panels 322, 324 are formed from the same or different material as foldable band 326. In some embodiments, opposing panels 322, 324 can be made of, at least in part, a plastic or paper material, e.g., wax paper. Opposing panels 322, 324 can comprise a substantially nonabsorbent material. In some embodiments, bag 300 can include a fragrance, a deodorizer, and/or an antimicrobial agent.

In some embodiments, a plurality of bags 300 are disposed in housing 230 and oriented such that foldable band 326 is coupled to front panel 322 and the front panel is closer to front end 230a of the housing than the opposing panel 324 is.

The above specification and examples provide a complete description of the structure and use of illustrative embodiments. Although certain embodiments have been described above with a certain degree of particularity, or with reference to one or more individual embodiments, those skilled in the art could make numerous alterations to the disclosed embodiments without departing from the scope of this invention. As such, the various illustrative embodiments of the devices are not intended to be limited to the particular forms disclosed. Rather, they include all modifications and alternatives falling within the scope of the claims, and embodiments other than the one shown may include some or all of the features of the depicted embodiment. For example, components may be omitted or combined as a unitary structure, and/or connections may be substituted. Further, where appropriate, aspects of any of the examples described above may be combined with aspects of any of the other examples described to form further examples having comparable or different properties and addressing the same or different problems. Similarly, it will be understood that the benefits and advantages described above may relate to one embodiment or may relate to several embodiments.

The claims are not intended to include, and should not be interpreted to include, means-plus- or step-plus-function limitations, unless such a limitation is explicitly recited in a given claim using the phrase(s) "means for" or "step for," respectively.

The invention claimed is:

1. A bag dispenser comprising:
    a housing that defines an interior volume and an opening and comprises an inner sleeve and an outer sleeve, where the outer sleeve is configured to move relative to the inner sleeve and to circumscribe the inner sleeve to form the housing;
    first and second guiderails spaced apart and parallel to each other, each guiderail comprising a supporting surface and disposed in the interior of the housing; and
    a plurality of bags disposed between the guiderails, where each of the bags comprises opposing side panels defining a mouth and a foldable band coupled to an upper portion of one of the opposing side panels adjacent the mouth, the foldable band extending between the guiderails and having first and second ends supported by a corresponding one of the supporting surfaces of the guiderails,
    wherein the foldable band is configured such that once folded it will retain its folded orientation.

2. The bag dispenser of claim 1, wherein the first and second guiderails are integrated into or supported by the inner sleeve.

3. The bag dispenser of claim 1, wherein the outer sleeve comprises a lid configured for moving to cover and uncover the opening of the housing.

4. The bag dispenser of claim 1, wherein the foldable band comprises a wire extending between the first end and the second end.

5. The bag dispenser of claim 1, wherein each of the bags is configured to receive a feminine hygiene product.

6. A method of using a bag dispenser comprising:
first and second guiderails spaced apart and parallel to each other, each guiderail comprising a supporting surface;
a plurality of bags disposed between the guiderails, where each of the bags comprises opposing side panels defining a mouth and a foldable band coupled to an upper portion of one of the opposing side panels adjacent the mouth, the foldable band extending between the guiderails and having first and second ends supported by a corresponding one of the supporting surfaces of the guiderails,
wherein the foldable band is configured such that once folded it will retain its folded orientation,
the method comprising removing one of the plurality of bags from the dispenser and placing a used hygiene product in the one of the plurality of bags and folding the foldable band to retain the used hygiene product therein.

7. The method of claim 6, wherein the foldable band comprises a wire extending between the first end and the second end.

8. A bag dispenser comprising:
first and second guiderails spaced apart and each extending between a rear-end and a front-end, wherein:
each of the guiderails comprises a guiding surface and a supporting surface, where the guiding surface extends along the supporting surface;
the first and second guiderails are disposed such that a first distance between the guiderails at their rear-ends is greater than a second distance between the guiderails at at least one point between the rear-ends and the front-ends; and
the guiding surfaces are configured to guide a bag and compress a portion of the bag as the bag is drawn toward the front-ends of the guiderails; and
first and second stops, each disposed along one of the first and second guiderails, a third distance between the first and second stops being less than the first distance and the first and second stops configured to resist sliding movement of a bag supported by the guiderails.

9. The dispenser of claim 8, where at least one of the first and second stops comprises a recess in a corresponding one of the guiding surfaces.

10. The dispenser of claim 8, further comprising a housing that defines an interior volume and an opening, where the first and second guiderails are disposed in the interior of the housing, where the opening is dimensioned to allow a bag to pass through the opening at a location between the stops and the rear-ends of the guiderails.

11. The dispenser of any of claim 10, where the housing comprises a first sidewall, an opposing a second sidewall, a base opposite the opening, where the first and second guiderails are integrated into or unitary with the respective sidewalls.

12. The dispenser of claim 10, where the opening is dimensioned to allow a bag to pass through the opening at a location between the stops and the rear-ends of the guiderails.

13. The dispenser of claim 10, wherein a portion of each of the supporting surfaces is movable relative to the housing.

14. The dispenser of claim 8, further comprising one or more bags disposed between the guiderails.

15. The dispenser of claim 14, where each of the bag(s) comprises opposing side panels defining a mouth and semi-rigid bands coupled to upper portions of the opposing side panels adjacent the mouth, the bands extending between the guiderails and having first and second ends supported by a corresponding one of the supporting surfaces of the guiderails.

16. The dispenser of claim 14, wherein each of the bag(s) has a width between 2 and 10 inches and a height between 2 and 10 inches.

17. The dispenser of claim 15, where the third distance is small enough to prevent straightening of the bands and thereby to hold the mouth of the bag open.

18. The dispenser of claim 15, further comprising at least a first bag and a second bag disposed between the stops and the rear-ends such that an opposing panel of the first bag is facing an opposing panel of the second bag, where the first bag is releasably coupled to the second bag.

19. The dispenser of claim 15, where each of the bag(s) includes a fragrance, an antimicrobial agent, or both.

20. The dispenser of claim 15, wherein each of the semi-rigid bands is made of cardboard.

* * * * *